US005119411A

United States Patent [19]

Nakamura

[11] Patent Number: 5,119,411

[45] Date of Patent: Jun. 2, 1992

[54] X-RAY OPTICAL APPARATUS

[75] Inventor: Hajime Nakamura, Kawasaki, Japan

[73] Assignee: Nikon Corporation, Tokyo, Japan

[21] Appl. No.: 632,941

[22] Filed: Dec. 24, 1990

[30] Foreign Application Priority Data

Jan. 10, 1990 [JP] Japan .................................. 2-1585

[51] Int. Cl.[5] .......................... A61B 6/08; G21K 7/00

[52] U.S. Cl. ...................................... 378/206; 378/43; 378/45; 378/53; 378/70; 378/84; 250/311

[58] Field of Search .................. 250/311; 378/206, 43, 378/45, 84, 701, 51, 53, 44

[56] References Cited

U.S. PATENT DOCUMENTS

| | | | |
|---|---|---|---|
| 2,843,751 | 7/1958 | Botty et al. | 378/43 |
| 2,877,353 | 3/1959 | Newberry | 378/43 |
| 4,317,036 | 2/1982 | Wang | 378/45 |
| 4,870,674 | 9/1989 | Schmahl et al. | 378/43 |
| 4,979,203 | 12/1990 | Suckewer et al. | 378/43 |

*Primary Examiner*—Janice A. Howell

*Assistant Examiner*—Kim-Kwok Chu

*Attorney, Agent, or Firm*—Shapiro and Shapiro

[57] ABSTRACT

An X-ray optical apparatus comprises an X-ray optical system which is capable of projecting an enlarged sample image by soft X-rays and a visible optical system to observe the sample with a visible radiation. To enable simultaneous observation using both optical systems, the systems utilize a common objective zone plate. The objective zone plate includes a base plate having an opening at the center thereof to pass the soft X-rays which have passed through the sample and also having a visible radiation passing section to the outside of the opening. A zone plate is supported centrally on the base plate for converging soft X-rays which have passed through the sample and forming the sample image at a predetermined position. An eyepiece is provided in a position displaced from the X-ray optical axis to enable visual observation of the sample with the light passed through the visible radiation transmitting section of the objective zone plate.

4 Claims, 4 Drawing Sheets

X-RAY OPTICAL APPARATUS

BACKGROUND OF THE INVENTION

1. Field of the Invention

The present invention relates to an X-ray optical apparatus, and more particularly, to an optical apparatus in which a part of an X-ray optical system and a part of a visible optical system are provided with the same optical axis.

2. Related Background Art

There is known an X-ray microscopic apparatus employing approximately 2 to 5 nm of wavelength and which can observe a living biological sample and the like enclosed in a sample capsule under higher power in comparison with an optical microscope.

Soft X-rays are those of which have normally not less than 200 pm of wavelength among X-rays having 1 pm to 10 nm of wavelength. Such soft X-rays are electromagnetic waves which are roughly two orders of magnitude shorter than a visible radiation having 400 to 800 nm of wavelength. Such X-rays can transmit through a substance surface without being reflected thereby. However, they can be well absorbed by the substance and have a property of being rapidly decayed even in the air. Accordingly, a transmission observation by the use of soft X-rays is generally conducted in an X-ray apparatus employing soft X-rays, wherein the optical path of the soft X-rays is maintained in a high degree of vacuum. The optical element employs Fresnel's zone pattern and extremely thin samples are generally used. FIG. 4 is a view illustrating an example of a conventional X-ray microscopic optical system equipped with an X-ray optical system and a visible optical system. In this optical microscope, a sample set in the microscope can be observed by the use of both optical systems, so that low power preliminary observation by a visible radiation or a combination of high resolution observation by soft X-rays and a color information observation by visible radiation can be conducted before observation under high power is conducted by soft X-rays.

In FIG. 4, an X-ray optical system 11, an observation sample S held in holder H and a part of visible optical system 12 are placed in a vacuum vessel 13. A part of an optical axis of the visible optical system 12 is constituted to coincide with an optical axis of the X-ray optical system which passes through the observation sample. The X-ray optical system 11 includes a soft X-ray generator G, a condenser zone plate R11, an objective zone plate R12 and a camera element C. The soft X-rays from the soft X-ray generator G can be converged on the observation sample S with condenser zone plate R11. An image of the observation sample S irradiated with the soft X-rays is formed on the image element C by the objective zone plate R12. The objective zone plate R12 is structurally similar to the condenser zone plate R11 and is shown in FIG. 5. This objective zone plate R12 is attached releasably on the optical axis and comprises a base plate W having a generally square aperture P at the center thereof for passing the soft X-rays, a thin silicon nitride membrane N covering the aperture P of the base plate W and the Fresnel's zone pattern (not shown) formed on this silicon nitride membrane N.

The visible optical system 12 includes a lamp B, a first condenser L11, a first mirror M11 and a second condenser lens L12 each having an aperture at the center thereof for passing the soft X-rays, an objective lens L13 and a second mirror M12 each having an aperture at the center thereof for passing the soft X-rays, a reticule r10 and an eyepiece L14. A luminous flux for illumination from a lamp B will be projected on the observation sample S through the first condenser lens L11, the first mirror M11 and the second condenser lens L12. The image of the observation sample S is provided by the luminous flux for illumination. This image is formed on the reticule r10 through the objective lens L13 and the second mirror M12 and can be observed through the eyepiece L14.

Conventional known objective zone plate R12, as shown in FIG. 5, can scarcely transmit the visible radiation. In the X-ray microscope in FIG. 4, the objective zone plate R12 is, therefore, attached to a slide frame for taking it into and from a visible radiation path, and which is retracted from the visible radiation path during observation by the visible optical system 12. Accordingly, such arrangement has the disadvantage of complex structure. In addition, in the X-ray optical system 11, there is provided a long light path with a fine soft X-ray beam. Positioning the objective zone plate R12 and angle adjusting thus require a relatively high precision. This, coupled with the fact that the mechanism of the objective zone plate must effect retracting and resetting of the zone plate R12 in a highly evacuated vessel 13, substantially increases the cost of the X-ray optical apparatus.

SUMMARY OF THE INVENTION

Accordingly, an object of the invention is to solve the disadvantages of the above conventional X-ray microscopic apparatus, and more particularly to provide an apparatus in which an objective zone plate is not required to retract from an optical axis during sample observation by visible optical system, which apparatus is readily operated and provides precise setting of the soft X-ray projection position of a sample.

This object is attained by providing an X-ray optical apparatus which comprises an X-ray optical system which is capable of projecting an enlarged sample image by soft X-rays, and a visible optical system which can observe the sample with a visible radiation, the X-ray optical system comprising:

a soft X-ray generator;

a condenser zone plate including a zone plate for converging soft X-rays from the X-ray generator and a base plate supporting the zone plate and having a soft X-ray passing opening at the center thereof; and an objective zone plate including a base plate having an opening at the center thereof to pass soft X-rays which have passed through the sample and having a visible radiation passing section to the outside of the opening, and a zone plate supported at the center of the base plate for converging soft X-rays which have passed through the sample and forming the sample image to a predetermined position;

the visible optical system comprising:

a visible radiation source displaced from the optical axis of the X-ray optical system;

a sample illumination means comprising a condenser lens having a soft X-ray passing opening at the center thereof to pass the X-rays converged by the condenser zone plate and condensing light from the visible radiation source so as to illuminate the sample;

an objective lens having a soft X-ray passing opening at the center thereof for passing the X-rays converged by the condenser zone plate, the optical axis thereof being arranged to coincide with the optical axis of the visible radiation in order that the visible radiation which passes through the sample also passes through the visible radiation passing section formed on the base plate of the objective zone plate; and an eyepiece displaced from the optical axis of the X-ray optical system for observing the sample image formed with the objective lens.

The X-ray optical apparatus is constructed as described above so that the objective zone plate is not necessary to retract from the optical axis of the X-ray optical system during sample observation and the soft X-ray projection position on the sample can be precisely defined. Accordingly, this invention has more simple construction, high positioning precision maintained for relatively long periods, and yet the treatment thereof is easy.

Other and further objects, and advantages of the invention will appear more fully from the following description referring to the accompanying drawings.

DESCRIPTION OF THE PREFERRED EMBODIMENTS

Figure 1:
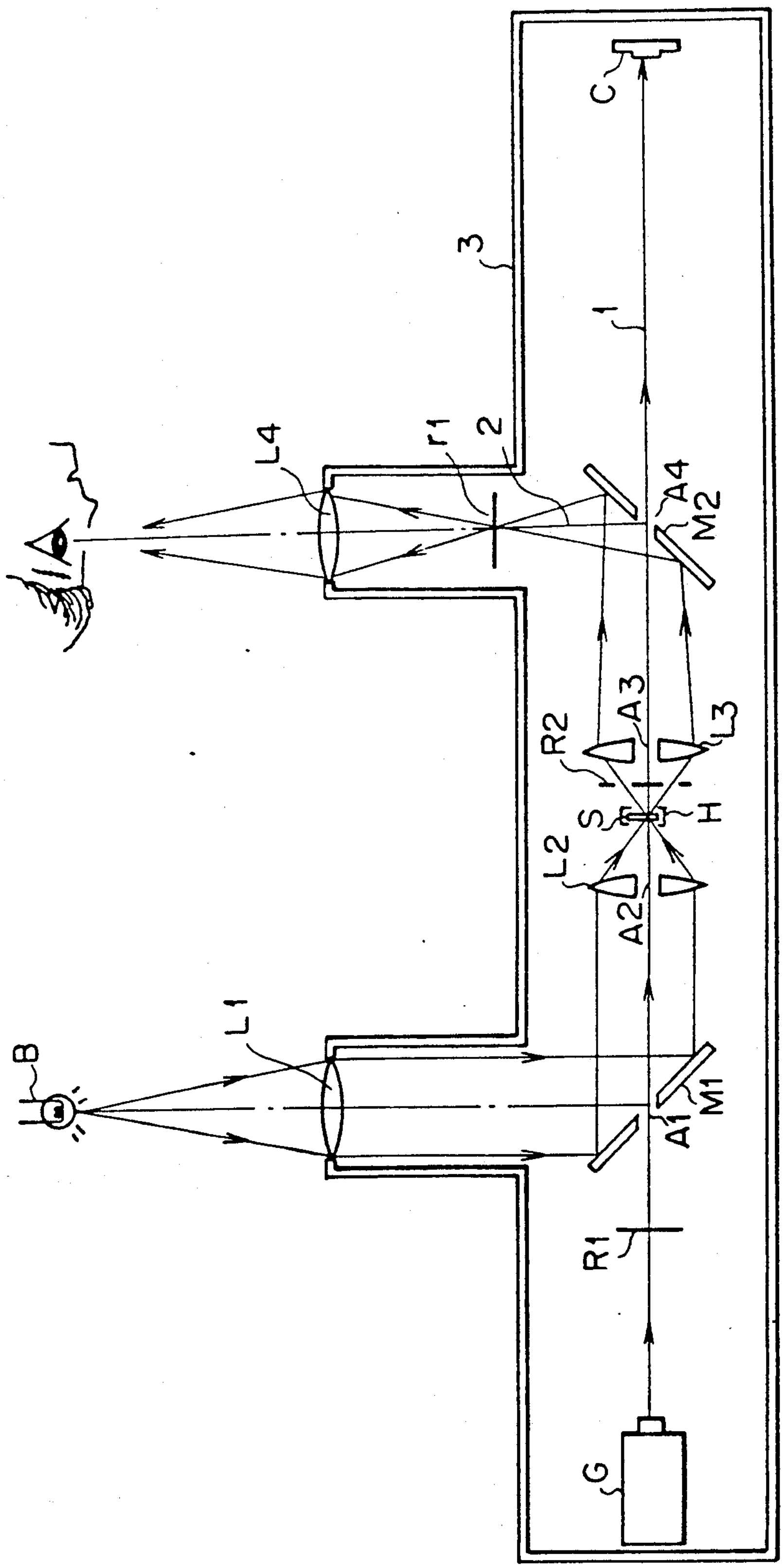
FIG. 1 is a schematic view illustrating a soft X-ray microscopic apparatus of an embodiment of the present invention.
Figure 2:
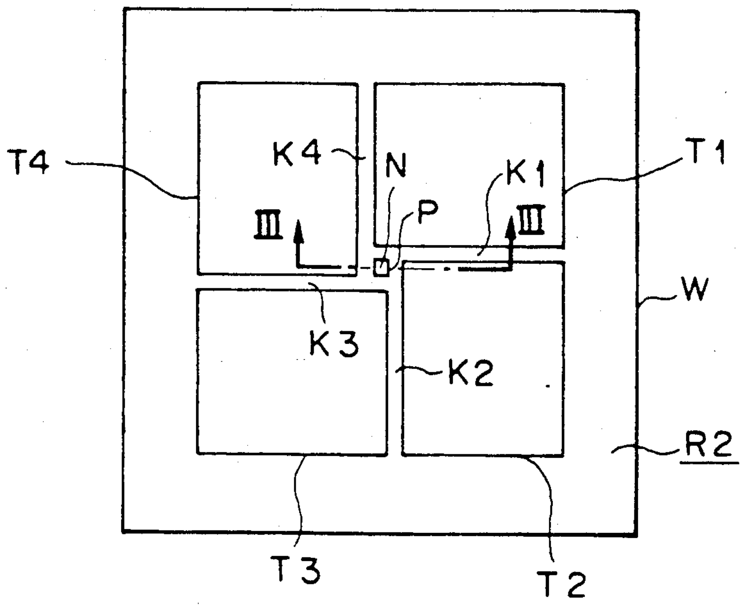
FIG. 2 is a plan view of an objective zone plate constituting a main part of the apparatus of the embodiment of the present invention.

Referring now to the drawings, FIG. 1 shows a schematic sectional view of a soft X-ray microscopic apparatus of an embodiment of the present invention. FIG. 2 is a plan view of an objective zone plate incorporated into the soft X-ray microscopic apparatus as illustrated in FIG. 1.

In FIG. 1, an observation sample S is provided in a central holder H. An X-ray optical system 1 is received in a vacuum vessel 3 in order to avoid attenuation of soft X-rays by the atmosphere. This optical system has a soft X-ray generator G, a condenser zone plate R1, an objective zone plate R2 which will be described in further detail, and a camera element C such as a CCD. The soft X-rays generated from the soft X-ray generator G are converged by the condenser plate R1 by the use of diffraction and are cast on the sample S. The soft X-rays diverge after transmission through the sample S and are converged on the camera element C by the objective zone plate R2 by the use of diffraction. The image of the portion of the sample S on which the soft X-rays are cast is projected on the camera element C. The respective zone plates R1 and R2 are not large size and convergence efficiencies to the soft X-rays are also low, so that the beam size of the soft X-rays on the sample S is approximately $\phi$0.2 mm. The light path from the soft X-ray generator to the camera element C attains 2 m.

A visible optical system 2 is superposed on part of the X-ray optical system 1 by the use of mirrors M1 and M2 having soft X-ray passing openings A1 and A4. This optical system 2 comprises a lamp B, a first condenser lens L1, a first mirror M1, a second condenser lens L2, an objective lens L3, a second mirror M2, a reticule r1 and an eyepiece L4. Soft X ray passing openings A2 and A3 are provided for the centers of the second condenser lens L2 and the objective lens L3 respectively.

In the second optical system 2, an optical lens has a large bore diameter and highly effective convergence in comparison with zone plates R1 and R2. The use of mirrors M1 and M2 notably allows for greater freedom of design as compared with the X-ray optical system including the zone plates R1 and R2. Lenses with their center portion open such as the condenser lens L2 and the objective lens L3 can be manufactured quite readily by those of ordinary skill.

An illumination light from the lamp B becomes a parallel light flux at the first condenser lens L1 and is reflected by the first mirror M1 provided at the optical axis of the X-ray optical system 1. Then, this illumination light is converged at the second condenser lens L2 and is cast on the sample S. The sample S lit by this illumination light is imaged on the reticule r1 through the objective lens L3 and the second mirror M2 and can be observed by the observer through the eyepiece L4.

Figure 3:
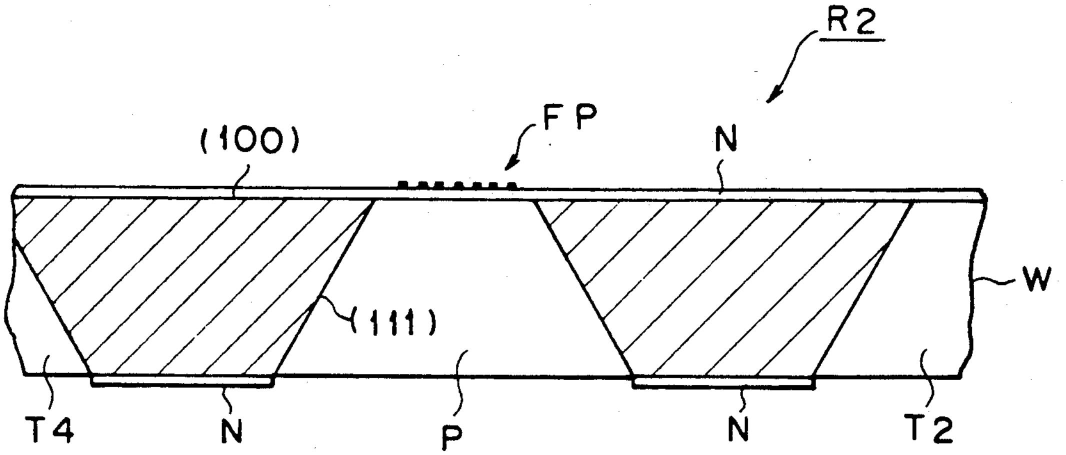
FIG. 3 is an expanded sectional view taken on line III—III of FIG. 2.
Figure 4:
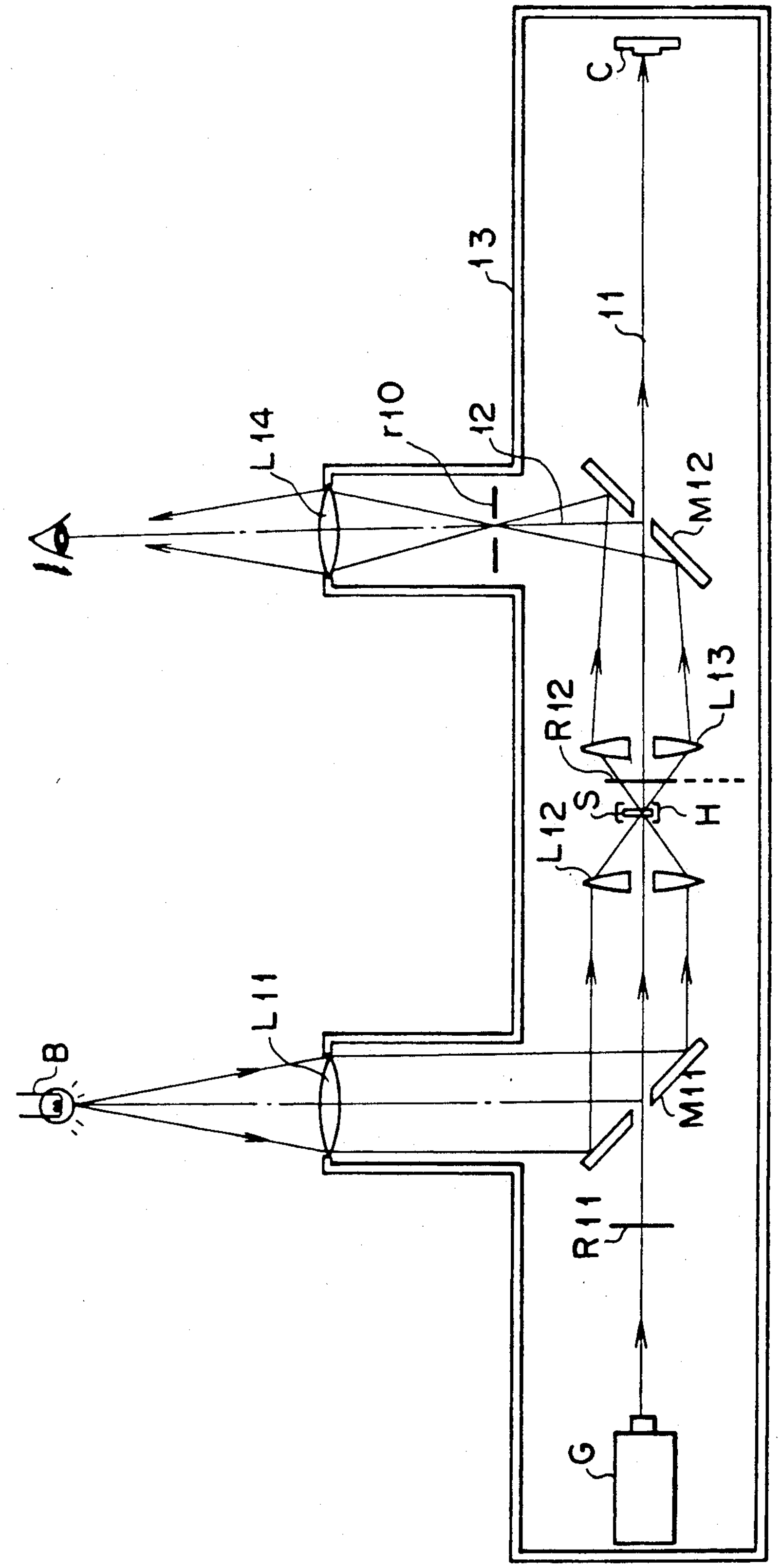
FIG. 4 Prior Art
FIG. 4 is a schematic view of a conventional soft X-ray microscopic apparatus.
Figure 5:
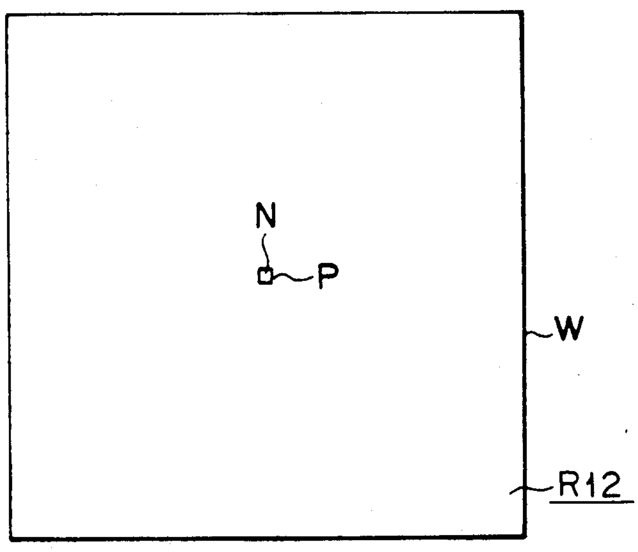
FIG. 5 is a plan view of a conventional zone plate provided for the soft X-ray microscopic apparatus as shown in FIG. 4.

The objective zone plate R2 has a soft X-ray passing opening P, as illustrated in FIG. 2 and FIG. 3, the zone plate comprising: a base plate W having four visible radiation passing openings T1 to T4 which surround this opening P; a thin membrane N to cover the central opening P; and Fresnel's zone pattern FP.

In FIG. 2, a base plate W is a square silicon plate having a thickness of 0.2 to 0.4 mm and respective sides of 14 mm. The plate W is provided with the square opening P having respective sides 0.2 mm for transmitting the soft X-rays at the center portion thereof. This opening P is covered with the thin silicon nitride membrane N. Fresnel's zone pattern FP is, as shown in FIG. 3, formed on the thin membrane. Visible radiation passing windows T1 to T4 of 5 mm$\times$5.5 mm are formed around the periphery of the opening P. As shown in FIG. 2, each window T1 to T4 is arranged with a long side thereof substantially opposed to a short side of another of the windows. The surface widths of the illustrative sides K1 to K4 are different at the front and rear surfaces thereof because sectional configuration of the sides is trapezoidal. The larger width is 0.5 mm.

In the objective zone plate R2 in this embodiment, Fresnel's zone pattern FP and visible radiation passing windows T1 to T4 are made integral with a sheet of silicon plate, so that positioning precision during formation of Fresnel's zone pattern FP enables achievement of the required optical system alignment precision during locating the objective zone plate R2. Furthermore, the objective zone plate R2 is fixed and not movable inside the X-ray microscopic apparatus, whereby the assembly and adjusting of the X-ray optical system becomes easy and initial alignment precision of the optical system is always maintained.

In the soft X-ray microscopic apparatus in FIG. 1 constructed as described above, the soft X-rays from the soft X-ray generator G are converged at the condenser zone plate R1, and are cast on the sample S through the soft X-ray passing openings A1 and A2 formed at the centers of the first mirror M1 and the second condenser lens L2 respectively. The X-rays which are transmitted through the sample S are converged at Fresnel's zone pattern $F_p$ formed at the center of the objective zone plate R2. These X-rays reach the camera element C through the soft X-ray passing openings A3 and A4 formed at the objective lens 3 and the second mirror M2 respectively. Accordingly, the portion of sample S image cast by the soft X-rays is formed on the camera element C.

In the visible optical system, the illumination light from the lamp B is converged at the first condenser lens L1 and reflected by the first mirror M1. This illumination light is further converged at the second condenser lens L2 and is cast on the sample S, so that the sample S is illuminated. Visible radiation from the illuminated sample S can pass four visible radiation passing openings T1 to T4 formed in the objective zone plate R2. The objective lens L3 converges the visible radiation which passes through the openings T1 to T4. Then, the objective lens L3 forms the sample S image on the reticule r1 through the second mirror M2. The sample image formed on this reticule r1 is observed through the eyepiece L4.

In the observational optical system ranging from the objective lens L3 to the eyepiece L4, the main optical axis passing the objective lens L3 is arranged to coincide with the main optical axis of the X-ray optical system 1. The soft X-ray projecting position can be readily located by moving the holder H in a plane perpendicular to the main axis while observing the sample through the eyepiece L4. The soft X-ray projecting image of the sample S located at such position can be readily formed on the camera element C.

A method of making objective zone plate R2 in this embodiment is now explained.

First, thin silicon nitride membranes ($Si_3N_4$) having a width of 0.05 to 0.1 μm are formed on the respective surfaces of the base plate W. The membrane producing method may be selected not only chemical methods such as LP-CVD (Low Pressure-Chemical Vapor Deposition) method, ECR-CVD (Electron Cyclotron Resonance-(Chemical Vapor Deposition)) method and the like, but also physical methods such as sputtering and the like. An internal stress of the membrane (pulling stress) is maintained in the range of $10^9$ to $10^{11}$ dyn/cm$^2$ in order to avoid slackening of the thin membrane N of the soft X-ray transmitting section and to maintain sufficient strength thereof.

Second, a photo resist layer is formed on the thin silicon nitride membrane. A mask exposure transfer, developing, and etching of the thin silicon nitride membrane are performed to remove thin silicon nitride membrane corresponding to one side of the opening P (bottom side in FIG. 3) and respective one sides of the windows T1 to T4 (bottom sides in FIG. 3). Either surface of the thin silicon nitride membranes N of the windows of T1 to T4 may be removed; however, a transparent silicon nitride membrane N remains at the windows of T1 to T4 in the finished zone plate.

Third, wet etching of the base plate W starts from the portion with thin silicon nitride membrane removed. The opening P and the windows of T1 to T4 are formed. The etching solution may employ a mixture of ethylenediamine, pyrocatechol and water, or potassium hydroxide solution. The silicon crystal board (100) employed as the base plate W can conduct anistropic etching and form a suitable tapering section automatically (a tapering surface is a surface 111 made of Si crystal) around the opening P.

Metal thin membranes such as Au, Cr, N and the like are formed on the thin silicon nitride membrane which remains on the opening P. The thin metal membrane is formed into the Fresnel's zone pattern, and the objective zone plate R2 is completed. Fresnel's zone pattern FP may be formed before the wet etching of the base plate W.

In the X-ray optical apparatus according to this invention, the visible radiation can freely pass through the objective zone while objective zone plate R2 is maintained in its predetermined position on the optical axis of the X-ray optical system. Therefore, both the X-ray optical system and the visible optical system can be used simultaneously, and the objective zone plate fixed inside the X-ray microscope maintains an initial positioning precision and does not require a mechanism for retraction and resetting thereof. Consequently, reliability of the X-ray optical system in this X-ray microscope increases and cost of production of the X-ray optical system decreases. The entire X-ray microscope can become smaller and operability thereof can be significantly improved.

Because the X-ray optical system and the visible optical system are simultaneously operative to obtain multiple information and the like, the invention offers a significantly enhanced range of application.

What is claimed is:

1. An X-ray optical apparatus having, in combination, an X-ray optical system which is capable of projecting an enlarged sample image by soft X-rays and a visible optical system which enables observation of said sample with visible radiation, said X-ray optical system comprising:

a soft X-ray generator;

a condenser zone plate for converging soft X-rays so as to cast them on said sample, including a zone plate for converging soft X-rays from said X-ray generator, and a base plate supporting said zone plate and having a first soft X-ray passing opening at the center thereof; and an objective zone plate including a base plate having a second soft X-ray passing opening at the center thereof to pass said soft X-rays which have passed through said sample and having a visible radiation passing section to the outside of said second soft X-ray passing opening, and a zone plate supported centrally of said base plate for converging soft X-rays which have passed through said sample and forming said sample image at a predetermined position;

said visible optical system comprising:

a visible radiation source displaced from the optical axis of said X-ray optical system;

sample illumination means comprising a condenser lens having a soft X-ray passing opening at the center thereof to pass said X-rays converged by said condenser zone plate, said condenser lens condensing light from said visible radiation source so as to illuminate said sample;

an objective lens having a soft X-ray passing opening at the center thereof for passing said X-rays converged by said condenser zone plate, the optical axis of said objective lens being arranged to coincide with the optical axis of said X-ray optical system in order that visible radiation which has passed through said sample passes through said visible radiation passing section of the base plate of said objective zone plate; and an eyepiece displaced from the optical axis of said X-ray optical system for observing a sample image formed with said objective lens; and wherein said visible radiation passing section of said objective zone plate is generally squarely formed by four rectangular openings with each of said four openings having a long side substantially opposed to a short side of another of said four openings at a predetermined distance, said second soft X-ray passing opening being surrounded substantially by said four rectangular openings.

2. An X-ray optical apparatus having, in combination, an X-ray optical system which is capable of projecting an enlarged sample image by soft X-rays and a visible optical system which enables observation of said sample with visible radiation, said X-ray optical system comprising:

a soft X-ray generator;

a condenser zone plate for converging soft X-rays so as to cast them on said sample, including a zone plate for converging soft X-rays from said X-ray generator, and a base plate supporting said zone plate and having a first soft X-ray passing opening at the center thereof; and an objective zone plate including a base plate having a second soft X-ray passing opening at the center thereof to pass said soft X-rays which have passed through said sample and having a visible radiation passing section to the outside of said second soft X-ray passing opening, and a zone plate supported centrally of said base plate for converging soft X-rays which have passed through said sample and forming said sample image at a predetermined position;

said visible optical system comprising:

a visible radiation source displaced from the optical axis of said X-ray optical system;

sample illumination means comprising a condenser lens having a soft X-ray passing opening at the center thereof to pass said X-rays converged by said condenser zone plate, said condenser lens condensing light from said visible radiation source so as to illuminate said sample;

an objective lens having a soft X-ray passing opening at the center thereof for passing said X-rays converged by said condenser zone plate, the optical axis of said objective lens being arranged to coincide with the optical axis of said X-ray optical system in order that visible radiation which has passed through said sample passes through said visible radiation passing section of the base plate of said objective zone plate; and an eyepiece displaced from the optical axis of said X-ray optical system for observing a sample image formed with said objective lens; and wherein the base plate of said objective zone plate is formed from a square silicon plate having sides of 14 mm and a thickness of 0.2 to 0.4 mm, and said zone plate of said objective zone plate comprises a silicon nitride membrane provided to cover said second soft X-ray passing opening and a Fresnel's zone pattern formed on said membrane.

3. An X-ray microscopic apparatus which enables observing an enlarged sample image by the use of soft X-rays and visible radiation, the apparatus comprising:

a soft X-ray generator;

a soft X-ray projecting optical element to converge soft X-rays from said soft X-ray generator so as to cast them on said sample;

a soft X-ray image formation optical element to converge soft X-rays which pass through said sample, so as to form said sample image in a predetermined position;

a camera element to transfer photoelectrically said sample image formed by said soft X-ray image forming optical element;

a visible radiation source displaced from an X-ray optical axis extending from said soft X-ray generator to said camera element;

sample illumination means comprising a condenser lens having a soft X-ray passing opening at the center thereof to pass said soft X-rays converged by said soft X-ray projection optical element, said condenser lens condensing light from said visible radiation source so as to irradiate said sample;

a base plate having an opening for passing soft X-rays which have passed through said sample, and including a central section supporting said soft X-ray image formation optical element and a visible light passing section having a plurality of visible light passing openings substantially surrounding said soft X-ray passing opening of said base plate;

an objective lens having a soft X-ray passing opening at the center thereof for passing said X-rays converged by said soft X-ray image formation optical element, and having an optical axis arranged to coincide with said X-ray optical axis in order that visible radiation which has passed through said sample passes through said visible radiation passing openings of said base plate; and an eyepiece displaced from said X-ray optical axis for observing a sample image formed with said objective lens; and wherein said visible light passing section of said base plate is generally squarely formed by four rectangular openings with each of said four openings having a long side substantially opposed to a short side of another of said four openings at a predetermined distance, said soft X-ray passing opening of said base plate formed in the center of said base plate and substantially surrounded by said four rectangular openings.

4. An X-ray microscopic apparatus which enables observing an enlarged sample image by the use of soft X-rays and visible radiation, the apparatus comprising:

a soft X-ray generator;

a soft X-ray projecting optical element to converge soft X-rays from said soft X-ray generator so as to cast them on said sample;

a soft X-ray image formation optical element to converge soft X-rays which pass through said sample, so as to form said sample image in a predetermined position;

a camera element to transfer photoelectrically said sample image formed by said soft X-ray image forming optical element;

a visible radiation source displaced from an X-ray optical axis extending from said soft X-ray generator to said camera element;

sample illumination means comprising a condenser lens having a soft X-ray passing opening at the center thereof to pass said soft X-rays converged by said soft X-ray projection optical element, said condenser lens condensing light from said visible radiation source so as to irradiate said sample;

a base plate having an opening for passing soft X-rays which have passed through said sample, and including a central section supporting said soft X-ray image formation optical element and a visible light passing section having a plurality of visible light passing openings substantially surrounding said soft X-ray passing opening of said base plate;

an objective lens having a soft X-ray passing opening at the center thereof for passing said X-rays converged by said soft X-ray image formation optical element, and having an optical axis arranged to coincide with said X-ray optical axis in order that visible radiation which has passed through said sample passes through said visible radiation passing openings of said base plate; and an eyepiece displaced from said X-ray optical axis for observing a sample image formed with said objective lens; and wherein said base plate is formed from a square silicon plate having side of 14 mm and a thickness of 0.2 to 0.4 mm said soft X-ray passing opening of said base plate is formed at the center of said base plate, and said soft X-ray image formation optical element supported by said base plate comprises a silicon nitride membrane provided to cover said soft X-ray passing opening formed at the center of said base plate and a Fresnel's zone pattern formed on said membrane.

* * * * *